United States Patent [19]

Ramey et al.

[11] 4,208,522

[45] * Jun. 17, 1980

[54] SUBSTITUTED PIPERAZINE DIONES

[75] Inventors: Chester E. Ramey, Spring Valley; John J. Luzzi, Carmel, both of N.Y.

[73] Assignee: Ciba-Geigy Corporation, Ardsley, N.Y.

[*] Notice: The portion of the term of this patent subsequent to Dec. 23, 1992, has been disclaimed.

[21] Appl. No.: 949,173

[22] Filed: Oct. 6, 1978

Related U.S. Application Data

[60] Continuation of Ser. No. 835,759, Sep. 22, 1977, Pat. No. 4,125,517, which is a division of Ser. No. 633,202, Nov. 19, 1975, Pat. No. 4,051,137, which is a division of Ser. No. 391,200, Aug. 24, 1973, Pat. No. 3,928,357, and a continuation-in-part of Ser. No. 237,982, Mar. 24, 1972, abandoned.

[51] Int. Cl.² ............................................ C07D 241/08
[52] U.S. Cl. ...................................................... 544/385
[58] Field of Search ........................................... 544/385

[56] References Cited

U.S. PATENT DOCUMENTS

| | | | |
|---|---|---|---|
| 3,318,876 | 5/1967 | Cignarella et al. | 260/240 |
| 3,928,357 | 12/1975 | Ramey et al. | 544/385 |
| 4,051,137 | 9/1977 | Ramey et al. | 544/385 |
| 4,125,517 | 11/1978 | Ramey et al. | 544/385 |
| 4,130,711 | 12/1978 | Shier | 544/385 |

*Primary Examiner*—Jose Tovar
*Attorney, Agent, or Firm*—Vincent J. Cavalieri; Luther A. R. Hall

[57] ABSTRACT

Substituted piperazine diones are stabilizers for synthetic polymeric materials normally subject to deterioration caused by ultraviolet light. The compounds are prepared by the alkylation reaction between a substituted piperazine dione and an organic halide. Polymeric compositions containing these stabilizers may also contain a hindered phenolic compound. A typical embodiment is 15,15'-dodecamethylenebis(7,15-diazadispiro[5,1,5,3]hexadecane-14,16-dione).

2 Claims, No Drawings

SUBSTITUTED PIPERAZINE DIONES

RELATED APPLICATION

This is a continuation of application Ser. No. 835,759 filed on Sept. 22, 1977 now U.S. Pat. No. 4,125,517 issued Nov. 14, 1978 which is a divisional of application Ser. No. 633,202 filed Nov. 19, 1975, now U.S. Pat. No. 4,051,137, which is a divisional of Ser. No. 391,200 filed Aug. 24, 1973, now U.S. Pat. No. 3,928,357, which is a continuation-in-part application Ser. No. 237,982, filed Mar. 24, 1972, now abandoned.

BACKGROUND OF THE INVENTION

This invention relates to the stabilization of organic material normally tending to deteriorate. In particular, the invention relates to the protection of synthetic polymers against the harmful degradative effects, such as discoloration and embrittlement caused by exposure to light, especially ultraviolet light.

It is known that actinic radiation, particularly in the near ultraviolet region, has a deleterious effect on both the appearance and properties of organic polymers. For example, normally colorless or light colored polyesters yellow on exposure to sunlight as do such cellulosics as cellulose acetate. Polystyrene discolors and cracks, with accompanying loss of its desirable physical properties when exposed to actinic light, while vinyl resins, such as polyvinyl chloride and polyvinyl acetate spot and degrade. The rate of air oxidation of polyolefins such as polyethylene and polypropylene is materially accelerated by ultraviolet light.

It has been proposed to stabilize polymeric materials against ultraviolet light deterioration by the use of various types of ultraviolet absorbers. Thus, U.S. Pat. No. 3,004,896 discloses for this purpose 2(2-hydroxyphenyl)benzotriazole derivatives, while U.S. Pat. No. 3,189,630 discloses certain metal salts of hydroxybenzoic acids which are useful as actinic stabilizers in synthetic polymers.

DETAILED DISCLOSURE

The present invention is directed to a class of ultraviolet light stabilizers which consist of a compound of the formula

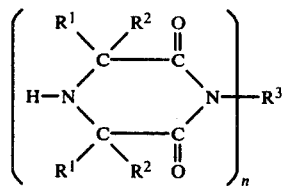

wherein
$R^1$ and $R^2$ are independently of each other methyl or ethyl or together with the carbon to which they are bound form a cyclopentyl or cyclohexyl ring, which is unsubstituted or substituted with a methyl group;
n is an integer of from 1 to 3;
when n is 1, $R^3$ is an alkyl group of from 1 to 20 carbon atoms or a benzyl group; when n is 2, $R^3$ is an alkylene group of from 1 to 20 carbon atoms, a p-xylylene group or an alkyl-substituted p-xylylene group, of the formula

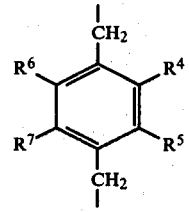

wherein
$R^4$, $R^5$, $R^6$ and $R^7$ is hydrogen or lower alkyl group containing from 1 to 5 carbon atoms;
when n is 3, $R^3$ is a 1,3,5-mesitylene group or a 2,4,6-alkyl substituted mesitylene group, of the formula

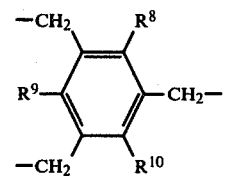

wherein
$R^8$, $R^9$ and $R^{10}$ are hydrogen or lower alkyl, containing from 1 to 5 carbon atoms.

By the term alkyl as represented by $R^1$ and $R^2$ is intended methyl or ethyl, with methyl being the preferred substituent. Representative of the cycloalkyl groups are cyclohexyl, cyclopentyl, 2-methyl, 3-methyl and 4-methylcyclohexyl, and 2-methyl and 3-methylcyclopentyl. The preferred cycloalkyl groups are cyclohexyl and 2-methylcyclohexyl.

This invention also relates to compositions of matter which are stabilized against ultraviolet light deterioration which comprises a synthetic organic polymer normally subject to ultraviolet deterioration containing from about 0.005% to 5% by weight of the polymer of the compounds of formula I and preferably from 0.01% to 2% by weight.

The piperazine dione derivatives as represented by formula I can be used in combination with other light stabilizers such as 2-(2-hydroxyphenyl)benzotriazoles, 2-hydroxybenzophenones, nickel complexes, and benzoates.

The stabilizers of this invention are suitable for the protection of many synthetic polymers from the deleterious effects of light. Homopolymers, copolymers, and mixtures thereof are embraced within the scope of substrates which may be stabilized with the stabilizers of this invention, along which may be mentioned, polystyrene and including homopolystyrene and copolymers with acrylonitrile and/or butadiene; vinyl resins formed from the polymerization of vinyl halides or from copolymerization of vinyl halides with unsaturated polymerizable compounds, for example, vinyl esters, $\alpha,\beta$-unsaturated acids, $\alpha,\beta$-unsaturated esters, and unsaturated hydrocarbons such as butadienes and styrene; poly-$\alpha$-olefins such as high and low density polyethylene, cross-linked polyethylene, polypropylene, poly(4-methyl-pentene-1), polybutene-1, and the like including copolymers of poly-$\alpha$-olefins such as ethylene-propylene copolymers, and the like; polybutadiene; polyisoprene; polyurethanes such as are prepared from polyols and organic polyisocyanate; polyamides such as hexamethylene-adipamide; polyesters such as polymethyleneterephthalates; polycarbonates such as those prepared from bisphenol-A and phosgene; polyacetals; polyethylene oxide; and polyacrylics such as polyacrylonitrile; polyphenyleneoxides such as those prepared from 2,6-dimethylphenol and the like. Particularly preferred polymers for the compositions of this invention are those normally solid polymers of alpha-olefins having up to 3 carbon atoms, e.g., ethylene-propylene and their copolymers.

The stabilized polymers of the present invention have utility in the normal uses for which plastics are employed and are particularly useful for film and fiber. Compounds of this invention may be incorporated in the polymeric substance during the usual processing operations, for example, by hot milling, the composition then being extruded, pressed, blow molded or the like into films, fibers, filaments, hollow spheres and the like. Where the polymer is prepared from a liquid monomer as in the case of styrene, the stabilizer may be dispersed or dissolved in the monomer prior to polymerization or curing.

In addition to the actinic stabilizers described, the plastic compositions may contain other additives such as plasticizers, pigments, fillers, dyes, glass or other fibers, thermal antioxidants, and the like. For example in most applications, it is desirable to incorporate into the resin composition, sufficient thermal antioxidants to protect the plastic against thermal and oxidative degradation. The amount of antioxidant required will be comparable to that of the actinic stabilizer. Namely, from about 0.005% to 5% and preferably from 0.01% to 2% by weight. Representative of such antioxidants are phosphite esters, such as triphenylphosphite and dibutylphosphite, and alkyl arylphosphites such as dibutylphenylphosphite, and the like.

The best results are obtained with the preferred class of thermal antioxidants, the hindered phenols. These compounds have been found to provide the best thermal stabilization with the least discoloration in the compositions of the invention. Typical of these phenolic antioxidants include the following:

(1) Phenolic compounds having the general formula

Q-(CH$_2$)$_2$-A wherein
Q is

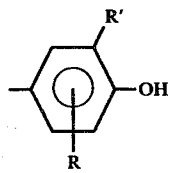

A is —CR(COOR'')$_2$

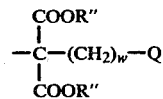

R is hydrogen or lower alkyl
R' is lower alkyl
R'' is alkyl group having from 6–24 carbon atoms
w is an integer from 0 to 4.

Illustrative examples of the compounds shown above are
di-n-octadecyl α-(3,5-di-t-butyl-4-hydroxybenzyl)malonate
di-n-octadecyl α-(3-t-butyl-4-hydroxy-5-methyl-benzyl)malonate which is disclosed in the Netherlands Pat. No. 6,711,199, Feb. 19, 1968
di-n-octadecyl-α,α'bis-(3-t-butyl-4-hydroxy-5-methylbenzyl)malonate which is disclosed in the Netherlands Pat. No. 6,803,498, Sept. 18, 1968.

(2) Phenolic compounds having the general formula

Q-R

Illustrative examples of the compounds shown above are
2,6-di-t-butyl-p-cresol
2-methyl-4,6-di-t-butylphenol and the like.

(3) Phenolic compounds having the formula

Q-C$_w$H$_{2w}$-Q 2,2'-methylene-bis(6-t-butyl-4-methylphenol)
2,2'-methylene-bis(6-t-butyl-4-ethylphenol)
4,4'-butylidene-bis(2,6-di-t-butylphenol)
4,4'-(2-butylidene)-bis(2-t-butyl-5-methylphenol)
2,2'-methylene-bis[6-(1-methylcyclohexyl)-4-methylphenol]
and the like.

(4) Phenolic compounds having the formula

R-O-Q

Illustrative examples of such compounds are
2,5-di-t-butylhydroquinone
2,6-di-t-butylhydroquinone
2,5-di-t-butyl-4-hydroxyanisole (5) Phenolic compounds having the formula

Q-S-Q

Illustrative examples of such compounds are
4,4'-thiobis-(2-t-butyl-5-methylphenol)
4,4'-thiobis-(2-t-butyl-6-methylphenol)
2,2'-thiobis-(6-t-butyl-4-methylphenol)

(6) Phenolic compounds having the formula

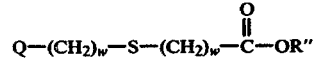

Illustrative examples of such compounds are
octadecyl-(3,5-dimethyl-4-hydroxybenzylthio)acetate
dodecyl-(3,5-di-t-butyl-4-hydroxybenzylthio)propionate (7) Phenolic compounds having the formula

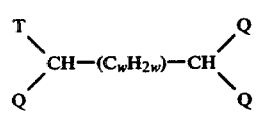

wherein T is hydrogen R or Q as defined above.
Illustrative examples of such compounds are
1,1,3-tris(3,5-dimethyl-4-hydroxyphenyl)-propane
1,1,3-tris(5-t-butyl-4-hydroxy-2-methylphenyl)butane
1,1,5,5-tetrakis-(3'-t-butyl-4'-hydroxy-6'-methylphenyl)-n-pentane (8) Phenolic compounds having the formula

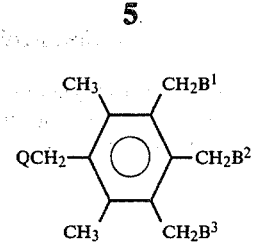

wherein $B^1$, $B^2$ and $B^3$ are hydrogen, methyl or Q, provided that when $B^1$ and $B^3$ are Q then $B^2$ is hydrogen or methyl and when $B^2$ is Q then $B^1$ and $B^3$ are hydrogen or methyl.

Illustrative examples of such compounds are 1,4-di(3,5-di-t-butyl-4-hydroxybenzyl)-2,3,5,6-tetramethylbenzene 1,3,5-tri(3,5-di-t-butyl-4-hydroxybenzyl)-2,4,6-trimethylbenzene (9) Phenolic compounds having the formula

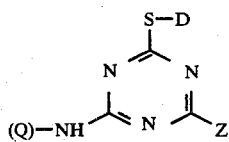

wherein

Z is NHQ, -S-D or -O-Q

D is alkyl group having from 6–12 carbon atoms or $-(C_wH_{2w})$-S-R''

Illustrative examples of such compounds are 2,4-bis-(n-octylthio)-6-(3,5-di-t-butyl-4-hydroxyaniline)-1,3,5-triazine 6-(4-hydroxy-3-methyl-5-t-butylanilino)-2,4-bis-(n-octylthio)-1,3,5-triazine 6-(4-hydroxy-3,5-dimethylanilino)-2,4-bis-(n-octylthio)-1,3,5-triazine 6-(4-hydroxy-3,5-di-t-butylanilino)-2,4-bis-(n-octylthioethylthio)-1,3,5-triazine 6-(4-hydroxy-3,5-di-t-butylanilino)-4-(4-hydroxy-3,5-di-t-butylphenoxy)-2-(n-octylthio)-1,3,5-triazine 2,4-bis(4-hydroxy-3,5-di-t-butylanilino)-6-(n-octylthio)-1,3,5-triazine.

The above phenolic triazine stabilizers are more fully described in U.S. Pat. No. 3,255,191.

(1) Phenolic compounds having the formula

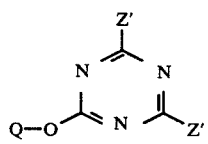

wherein Z' is -O-Q, -S-D or -S-$(C_wH_{2w})$-SD

Illustrative examples of such compounds are 2,3-bis-(3,5-di-t-butyl-4-hydroxyphenoxy)-6-(n-octylthio)-1,3,5-triazine 2,4,6-tris-(4-hydroxy-3,5-di-t-butylphenoxy)-1,3,5-triazine.

6-(4-hydroxy-3,5-di-t-butylphenoxy)-2,4-bis-(n-octylthioethylthio)-1,3,5-triazine 6-(4-hydroxy-3-methylphenoxy)-2,4-bis-(n-octylthio)-1,3,5-triazine 6-(4-hydroxy-3-t-butylphenoxy)-2,4-bis-(n-octylthioethylthio)-1,3,5-triazine 6-(4-hydroxy-3-methyl-5-t-butylphenoxy)-2,4-bis-(n-octylthio)-1,3,5-triazine 2,4-bis-(4-hydroxy-3-methyl-5-t-butylphenoxy)-6-(n-octylthio)-1,3,5-triazine 2,4,6-tris-(4-hydroxy-3-methyl-5-t-butylphenoxy)-1,3,5-triazine 6-(4-hydroxy-3,5-di-t-butylphenoxy)-2,4-bis-(n-octylthiopropylthio)-1,3,5-triazine 6-(4-hydroxy-3,5-di-t-butylphenoxy)-2,4-bis-(n-dodecylthioethylthio)-1,3,5-triazine 2,4-bis-(4-hydroxy-3,5-di-t-butylphenoxy)-6-butylthio-1,3,5-triazine 2,4-bis-(4-hydroxy-3,5-di-t-butylphenoxy)-6-(n-octadecylthio)-1,3,5-triazine 2,4-bis-(4-hydroxy-3,5-di-t-butylphenoxy)-6-(n-dodecylthio)-1,3,5-triazine 2,4-bis-(4-hydroxy-3,5-di-t-butylphenoxy)-6-(n-octylthiopropylthio)-1,3,5-triazine 2,4-bis-(4-hydroxy-3,5-di-t-butylphenoxy)-6-(n-octylthioethylthio)-1,3,5-triazine 2,4-bis-(4-hydroxy-3,5-di-t-butylphenoxy)-6-(n-dodecylthioethylthio)-1,3,5-triazine.

The above phenolic triazine stabilizers are more fully described in U.S. Pat. No. 3,255,191.

(11) Phenolic compounds having the formula

[Q-C$_z$H$_{2z}$—COO—C$_{\bar{z}}$H$_{2\bar{z}}$]$_p$R'''-(R)$_{4-p}$ wherein p is an integer from 2 to 4 and R''' is a tetravalent radical selected from aliphatic hydrocarbons having from 1 to 30 carbon atoms aliphatic mono and dithioethers having from 1 to 30 carbon atoms aliphatic mono and diethers having from 1 to 30 carbon atoms and z is an integer from 0 to 6.

Illustrative examples of such compounds are

Sub-class I n-Octadecyl 3-(3,5-di-t-butyl-4-hydroxyphenyl)-propionate n-Octadecyl 2-(3,5-di-t-butyl-4-hydroxyphenyl)-acetate n-Octadecyl 3,5-di-t-butyl-4-hydroxybenzoate n-Hexyl 3,5-di-t-butyl-4-hydroxyphenylbenzoate n-Dodecyl 3,5-di-t-butyl-4-hydroxyphenylbenzoate Neo-dodecyl 3-(3,5-di-t-butyl-4-hydroxyphenyl)propionate Dodecyl β-(3,5-di-t-butyl-4-hydroxyphenyl)propionate Ethyl α-(4-hydroxy-3,5-di-t-butylphenyl)-isobutyrate Octadecyl α-(4-hydroxy-3,5-di-t-butylphenyl)isobutyrate Octadecyl α-(4-hydroxy-3,5-di-t-butylphenyl)propionate Sub-class II 2-(n-octylthio)ethyl 3,5-di-t-butyl-4-hydroxybenzoate 2-(n-octylthio)ethyl 3,5-di-t-butyl-4-hydroxyphenylacetate 2-(n-octadecylthio)ethyl 3,5-di-t-butyl-4-hydroxyphenylacetate 2-(n-octadecylthio)ethyl 3,5-di-t-butyl-4-hydroxy benzoate 2-(2-hydroxyethylthio)ethyl 3,5-di-t-butyl-4-hydroxybenzoate 2,2'-Thiodiethanol bis(3,5-di-t-butyl-4-hydroxyphenyl)acetate Diethyl glycol bis-[3,5-di-t-butyl-4-hydroxyphenyl)propionate]
2-(n-octadecylthio)ethyl 3-(3,5-di-t-butyl-4-hydroxyphenyl)propionate
2,2'-Thiodiethanol-bis-3-(3,5-di-t-butyl-4-hydroxyphenyl)propionate
Stearamido N,N-bis-[ethylene 3-(3,5-di-t-butyl-4-hydroxyphenyl)propionate]
n-Butylimino N,N-bis-[ethylene 3-(3,5-di-t-butyl-4-hydroxyphenyl)propionate]
2-(2-stearoyloxyethylthio)ethyl 3,5-di-t-butyl-4-hydroxybenzoate
2-(2-hydroxyethylthio)ethyl 7-(3-methyl-5-t-butyl-4-hydroxyphenyl)heptanoate
2-(2-stearoyloxyethylthio)ethyl 7-(3-methyl-5-t-butyl-4-hydroxyphenyl)heptanoate Sub-class III 1,2-propylene glycol bis-[3-(3,5-di-t-butyl-4-hydroxyphenyl)propionate]
Ethylene glycol bis-[3-(3,5-di-t-butyl-4-hydroxyphenyl)propionate]
Neopentylglycol bis-[3-(3,5-di-t-butyl-4-hydroxyphenyl)propionate]
Ethylene glycol bis-(3,5-di-t-butyl-4-hydroxyphenylacetate)
Glycerine-1-n-octadecanoate-2,3-bis-(3,5-di-t-butyl-4-hydroxyphenylacetate
Pentaethylthritol-tetrakis-[3-(3',5'-di-t-butyl-4'-hydroxyphenyl)propionate]
1,1,1-trimethylol ethane-tris-3-(3,5-di-t-butyl-4-hydroxyphenyl)propionate
Sorbitol hexa-[3-(3,5-di-t-butyl-4-hydroxyphenyl)propionate]
1,2,3-butanetriol tris-[3-(3,5-di-t-butyl-4-hydroxyphenyl)propionate]
2-hydroxyethyl 7-(3-methyl-5-t-butyl-4-hydroxyphenyl)heptanoate
2-stearoyloxyethyl 7-(3-methyl-5-t-butyl-4-hydroxyphenyl)heptanoate
1,6-n-hexanediol-bis[(3',5'-di-t-butyl-4-hydroxyphenyl)propionate]

The above phenolic ester stabilizers of sub-classes I, II and III are more fully described in U.S. Pat. Nos. 3,330,859, and 3,644,482, respectively.

(12) Phenolic compounds having the formula

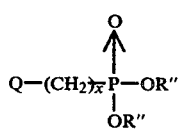

where x is an integer of 1 ro 2.
Illustrative examples of such compounds are
Di-n-octadecyl 3,5-di-t-butyl-4-hydroxybenzylphosphonate
Di-n-octadecyl 3-t-butyl-4-hydroxy-5-methylbenzylphosphonate
Di-n-octadecyl 1-(3,5-di-t-butyl-4-hydroxyphenyl)-ethanephosphonate
Di-n-tetradecyl 3,5-di-t-butyl-4-hydroxybenzylphosphonate
Di-n-hexadecyl 3,5-di-t-butyl-4-hydroxybenzylphosphonate
Di-n-docosyl-3,5-di-t-butyl-4-hydroxybenzylphosphonate
Di-n-octadecyl-3,5-di-t-butyl-4-hydroxybenzylphosphonate The above di-(higher)alkyl phenolic phosphonates are more fully described in U.S. Pat. No. 3,281,505.

(13) Phenolic compounds having the formula

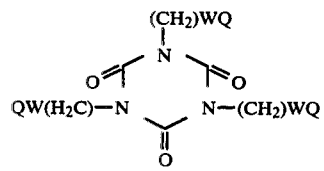

wherein W and Q are as defined above.
Illustrative examples of such compounds are
tris-(3,5-di-t-butyl-4-hydroxybenzyl)isocyanurate
tris-(3-t-butyl-4-hydroxy-5-methylbenzyl)isocyanurate
The above hydroxyphenylalkenyl isocyanurates are more fully described in U.S. Pat. No. 3,531,483.

The above phenolic hydrocarbon stabilizers are known and many are commercially available.

While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.

The compounds of this invention may be prepared by reacting a substituted piperazine dione of the formula

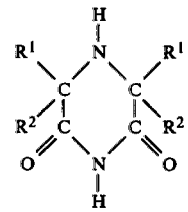

wherein $R^1$ and $R^2$, are as defined above with a organic mono, di or tri-halo compound. The alkylation reaction is carried out by first preparing the alkali or alkaline earth metal salt of the compound of formula II and reacting the resulting salt with the appropriate organic halide in a solvent such as dimethylformamide, isopropanol or acetone at about 75° C.

Compounds of formula II, wherein $R^1$ and $R^2$ form a mono cyclic ring with the carbon to which they are attached, may be prepared by the self condensation of a cycloalkyl amino cyanohydrin according to the procedure described by R. Sudo and S. Ichihera, Bull, Chem. Soc. Japan 36 34 (1963) and subsequent hydrolysis as described by E. F. J. Duynstee et al, Recueil de Chemie des Pays - Bas 87 945 (1968). The cycloalkylamino cyanohydrin is formed by the sequential addition of hydrogen cyanide and ammonia to a cycloalkanone as described by W. E. Noland, R. J. Sundberg and M. L. Michaelson, J. Org. Chem. 28 3576 (1963). Although the above references deal specifically with the cycloalkyl case, the procedures therein have been found to be operable in the alkyl case as well, for example substitution of an alkanone such as acetone for the cycloalkanone such as cyclohexanone in the above procedure.

Examples of organic halides which can be reacted with the salts of the compounds of formula II include organic monohalides such as methyliodide, ethyl chloride, propyl bromide, isopropyl chloride, butyl bromide, pentyl bromide, isopentyl chloride, hexyl bromide, octyl bromide, dodecyl bromide, tetradecyl chloride, hexadecyl bromide, octadecyl bromide, eicosyl bromide, benzyl chloride and the like; organic dihalides such as methylene bromide, dibromoethane, 1,3-dibromopropane, 1,3-dibromobutane, 1,4-dibromobutane, 1,8-dibromooctane, 1,12-dichlorododecane, 1,2-dichlorooctane, 1,18-dibromooctadecane, 1,20-dibromoeicosane, p-dichloroxylilene, 2,3,5,6-tetramethyl-1,4-bis-chloromethylbenzene and the like; organic trihalides such as $\alpha,\alpha',\alpha''$-trichloromesitylene, 2,4,6-trimethyl-$\alpha,\alpha',\alpha''$-trichloromesitylene, 1,2,3-tribromobutane and the like. The preferred organic monohalide contains from 6 to 18 carbon atoms. The preferred organic dihalide contains from 2 to 12 carbon atoms and the preferred organic trihalide contains from 4 to 12 carbon atoms.

The following examples, presented for illustration and not limitation, will further serve to typify the nature of the present invention.

EXAMPLE 1

1-Aminocyclohexanecarbonitrile

In a 200 ml—3 necked flask equipped with a stirrer, thermometer, condenser drying tube and gas inlet tube were placed 100 g (0.8 moles) of cyclohexanone cyanohydrin and the reaction mixture was cooled with an ice bath to 15° C. Gaseous anhydrous ammonia was introduced to the reaction mixture through the gas inlet tube for 6 hours. The reaction was then stopped and allowed to stand overnight.

The next day anhydrous ammonia was again passed through the reaction mixture for 5 hours at 25° C. then dry $N_2$ was passed through the reaction mixture to entrain any excess $NH_3$. The product was then dissolved in 250 ml of benzene, the benzene solution washed two times with 250 ml of water, and the solution dried over anhydrous $Na_2SO_4$. Evaporation of the benzene yielded the product which was a slightly yellow oil.

In a similar manner, 1-aminoisobutyronitrile was prepared by substituting for cyclohexanone cyanohydrin an equivalent amount of acetone cyanohydrin.

Similarly, 1-amino-2-methyl cyclohexane carbonitrile is prepared by substituting for cyclohexanone cyanohydrin an equivalent amount of 2-methyl cyclohexanone cyanohydrin.

EXAMPLE 2

Bis-(1-cyanocyclohexyl)amine

In a 1-necked round bottomed flask equipped with a capillary nitrogen inlet and an air condenser was placed 48.2 g (0.39 moles) of 1-aminocyclohexane carbonitrile. The reaction mixture was heated in an oil bath to a bath temperature of 75°–100° over 1 hour and placed under a vacuum using a water aspirator. The reaction was continued for 24 hours, cooled to room temperature, the vacuum released, and the crystalline mass was triturated with ether and filtered by suction, yielding 19.1 g of white crystals, m.p. 133°–138° C.

In a similar manner, bis(1-cyanoisopropylamine) was prepared by substituting for 1-aminocyclohexane carbonitrile an equivalent amount of 1-aminoisobutyronitrile.

Similarly, bis-(1-cyano-2-methyl cyclohexyl) amine is prepared by substituting for 1-aminocyclohexanecarbonitrile an equivalent amount of 1-amino-2-methyl cyclohexanecarbonitrile.

EXAMPLE 3

7,15-diazadispiro[5,1,5,3]hexadecane-14,16-dione

To 406 g of 96% $H_2SO_4$ contained in a 500 ml 3-necked flask equipped with a stirrer, thermometer and powder funnel was added with stirring and cooling, 30.0 g of powdered bis-(1-cyanocyclohexyl)amine over about a 2 hour period. The temperature of the reaction mixture was maintained at 0°–5° during the addition by using an ice bath. The reaction mixture was allowed to warm to room temperature and to stir overnight. The reaction mixture was then heated to 100° C. for one hour, then cooled to approximately 15° C. and poured onto 3000 g. of ice. The aqueous mixture was neutralized to pH 7 by the addition of approximately 800 ml of 10 N NaOH. The resulting precipitate was collected by suction filtration, washed well with water, and dried in a vacuum oven, yielding a white powder, m.p. 155°–160° C.

In a similar manner, 2,2,6,6-tetramethyl-3,5-diketopiperazine was prepared by substituting for bis(1-cyanohexyl)amine an equivalent amount of bis(1-cyanoisopropylamine).

Similarly, 1,9-dimethyl-7,15-diazadispiro[5,1,5,3]hexadecane-14,16-dione is prepared by substituting for bis-(1-cyanocyclohexyl)amine an equivalent amount of bis-(1-cyano-2-methylcyclohexyl)amine.

EXAMPLE 4

15-n-octadecyl-7,15-diazadispiro[5,1,5,3]hexadecane-14,16-dione

To a solution of 10.0 g. (0.04 moles) of 7,15-diazadispiro[5,1,5,3]hexadecane-14,16-dione in 150 ml of anhydrous methanol in a 500 ml flask was added 2.6 g. of 86% KOH (0.04 moles) and the mixture was shaken until solution was obtained. The reaction mixture was then evaporated to dryness under reduced pressure. The residue was transferred to a 300 ml 3-necked flask equipped with a stirrer, thermometer, condenser with drying tube, dropping funnel and nitrogen inlet with the aid of a small amount of dry DMF. To the potassium imide salt, under a nitrogen atmosphere, was added 150 ml of dry DMF. To the stirred solution was added dropwise a solution of 13.3 g. (0.04 moles) of n-octadecyl bromide in 50 ml of DMF. The reaction mixture was heated slowly to 75° C. and held at that temperature for 3 hours. The reaction mixture was cooled and allowed to stand at room temperature overnight. The reaction mixture was then taken up in 500 ml ether, the ether solution washed well with water, dried over anhydrous $Na_2SO_4$ and evaporated under reduced pressure. The residue, which crystallized on standing, was recrystallized from methanol yielding 14.3 g. of white needles as the product, m.p. 39°–40° C.

By following the above procedure, and substituting for the n-octadecylbromide an equivalent amount of:
(a) benzyl chloride
(b) 2,3,5,6-tetramethyl-p-dichloroxylilene
(c) 1,12-dibromdodecane
(d) 1,3,5-trimethyl-2,4,6-trischloromethylbenzene
(e) 1,8-dibromooctane
(f) 1,4-dibromobutane
(g) methyliodide
(h) octyl bromide
(i) methylene dibromide (j) 1,16-dibromohexadecane
there is respectively obtained the following compounds:
(a) 15-benzyl-7,15-diazadispiro[5,1,5,3]hexadecane-14,16-dione, m.p. 91°–94° C.
(b) 15,15'-(2",3",5",6"-tetramethyl p-xylilidenyl) bis(7,15-diazadispiro[5,1,5,3]hexadecane-14,16-dione), m.p. 253°–257° C.
(c) 15,15'-n-dodecanemethylene bis(7,15-diazadispiro[5,1,5,3]hexadecane-14,16-dione), m.p. 100°–103° C.
(d) 15,15',15"-(2,4,6-trimethyl α,α',α"-mesitylidene) tris-(7,15-diazadispiro[5,1,5,3]hexadecane-14,16-dione, m.p. 236°–240° C.
(e) 15,15'-n-octamethylene bis(7,15-diazadispiro[5,1,5,3]hexadecane-14,16-dione)
(f) 15,15'-tetramethylene bis(7,15-diazadispiro[5,1,5,3]hexadecane-14,16-dione, m.p. 178°–181° C.
(g) 15-methyl-7,15-diazadispiro[5,1,5,3]hexadecane-14,16-dione, m.p. 122°–126° C.
(h) 15-n-octyl-7,15-diazadispiro[5,1,5,3]hexadecane-14,16-dione)
(i) 15,15'-methylene bis(7,15-diazadispiro[5,1,5,3]hexadecane-14,16-dione), m.p. 209°–215° C.
(j) 15',15'-hexadecamethylene bis(7,15-diazadispiro[5,1,5,3]hexadecane-14,16-dione), m.p. 82°–87° C.

EXAMPLE 5

By essentially following the procedure of Example 4 and substituting for 7,15-diazadispiro[5,1,5,3]hexadecane-14,16-dione in each compound prepared in the example an equivalent amount of 2,2,6,6-tetramethyl-3,5-diketopiperazine, there is respectively obtained the following compounds:
(a) 4-n-octadecyl-2,2,6,6-tetramethyl-3,5-diketopiperazine; m.p. 52°–54° C.
(b) 4-benzyl-2,2,6,6-tetramethyl-3,5-diketopiperazine; m.p. 80°–84° C.
(c) 4,4'(2",3",5",6"-tetramethyl-p-xylilidenyl) bis(2,2,6,6-tetramethyl-3,5-diketopiperazine
(d) 4,4'-(n-dodecamethylene)bis(2,2,6,6-tetramethyl-3,5-diketopiperazine; m.p. 73°–75° C.
(e) 4,4'-(2,4,6-trimethyl α,α',α"-mesitylidene) tris(2,2,6,6-tetramethyl-3,5-diketopiperazine)
(f) 4,4'(n-octamethylene)bis(2,2,6,6-tetramethyl-3,5-diketopiperazine)
(g) 4,4'(tetramethylene)bis(2,2,6,6-tetramethyl-3,5-diketopiperazine)
(h) 4-methyl-2,2,6,6-tetramethyl-3,5-diketopiperazine
(i) 4-n-octyl-2,2,6,6-tetramethyl-3,5-diketopiperazine

EXAMPLE 6

By essentially following the procedure of Example 4 and substituting for 7,15-diazadispiro[5,1,5,3]hexadecane-14,16-dione and the organic halides used in the example, an equivalent amount of 1,9-dimethyl-7,15-diazadispiro[5,1,5,3]hexadecane 14,16-dione and n-octadecylbromide there is obtained 15-n-octadecyl-1,9-dimethyl-7,15-diazadispiro[5,1,5,3]hexadecane.

EXAMPLE 7

Artificial Light Exposure Test

Deterioration of most polymers caused by ultraviolet light is so slow at ambient temperatures, even in the absence of stabilizers, that testing of the effects of stabilizers generally must be conducted either at higher temperatures or in an accelerated artificial light exposure device in order to yield results in a convenient period of time. The test conducted on polymers using an artificial light exposure device is described below:

(a) Sample Preparation 5 mil Film—Unstabilized polypropylene powder (Hercules Profax 6501) is thoroughly blended with the indicated amounts of additives. The blended material is then milled on a two roll mill for 5 minutes at 182° C. The milled sheet is then compression molded at 220° C. into 5 mil thick film under a pressure of 175 psi and water cooled in the press.

(b) Testing Method

This test is conducted in a FS/BL unit, basically of the American Cyanamid design, which consists of 40 tubes of alternating fluorescent sun lamps and black lights (20 of each). The 5 mil sample films are mounted on 3×2" IR card holders with ¼"×1" windows and are placed on a rotating drum 2 inches from the bulbs in the FS/BL unit. The time in hours is noted for the development of 0.5 carbonyl absorbance units as determined on an Infrared Spectrophotometer. The development of carbonyl functional groups in the polymer is proportional to the amount of degradation caused by the ultraviolet light exposure.

The test results reported below were obtained according to the procedures described above. The amounts of the additives are expressed in weight percent based on the weight of the polymer.

Table I

| Formulation* | Time in Hours to .5 Carbonyl Absorbance Units |
|---|---|
| .5% 15-n-octadecyl-7,15-diazadispiro [5,1,5,3]hexadecane-14,16-dione | 855 |
| .5% 15-benzyl-7,15-diazadispiro [5,1,5,3]hexadecane-14,16-dione | 725 |
| .5% 15,15'-(2",3",5",6"-tetramethyl p-xylilidenyl)bis(7,15-diazadispiro [5,1,5,3]hexadecane 14,16-dione | 340 |
| .5% 15,15'-n-dodecanemethylene bis (7,15-diazadispiro[5,1,5,3]hexadecane 14,16-dione) | 680 |
| .5% 15,15'-n-octamethylene bis(7,15-diazadispiro[5,1,5,3]hexadecane 11,16-dione) | 620 |
| .5% 15,15',15"-(2,4,6-trimethyl-α,α',α"-mesitylidene)tris(7,15-diazadispiro [5,1,5,3]hexadecane-14,16-dione | 410 |
| .5% 15,15'-tetramethylene bis(7,15-diazadispiro[5,1,5,3]hexadecane-14,16-dione) | 713 |
| .5% 4-n-octadecyl-2,2,6,6-tetramethyl-3,5-diketo piperazine | 830 |
| .5% 15-methyl-7,15-diazadispiro[5,1,5,3] hexadecane-14,16-dione | 750 |
| .5% 15-n-octyl-7,15-diazadispiro [5,1,5,3]hexadecane-14,16-dione | 1170 |
| 0.5% 4-benzyl-2,2,6,6-tetramethyl-3,5-diketopiperazine | 800 |
| 0.5% 4,4'-n-dodecamethylene bis (2,2,6,6-tetramethyl-3,5-diketopiperazine) | 1040 |
| 0.5% 15,15'-methylene bis(7,15-diazadispiro[5,1,5,3]hexadecane-14,16-dione) | 720 |
| 0.5% 15,15'-hexadecamethylene bis (7,15-diazadispiro[5,1,5,3] hexadecane-14,16-dione) | 1005 |
| Control* | 225 |

*Each of the samples tested and the control contains 0.2% of (di-n-octadecyl(3,5-di-t-butyl-4-hydroxybenzyl)phosphonate which is an antioxidant which prevents oxidative degradation of polypropylene.

Other hindered phenolic antioxidants may be used in place of di-octadecyl(3,5-di-t-butyl-4-hydroxybenzyl)- phosphonate in the above mentioned compositions for example, di-n-octadecyl α-(3-t-butyl-4-hydroxy-5-methylbenzyl)malonate, 2,4-bis-(n-octylthio)-6-(3,5-di-t-butyl-4-hydroxyanilino)-1,3,5-triazine, octadecyl 3-(3',5'-di-t-butyl-4'-hydroxyphenyl)propionate, pentaethylthritol-tetrakis[3-(3,5-di-t-butyl-4-hydroxyphenyl)-propionate], tris-(3,5-di-t-butyl-4-hydroxybenzyl-)isocyanurate respectively.

EXAMPLE 8

(a) A composition comprising acrylonitrilebutadienestyrene terpolymer and 1% by weight of 15,15'-n-dodecamethylene bis(7,15-diazadispiro[5,1,5,3]hexadecane-14,16-dione) resists embrittlement due to exposure to ultraviolet light longer than one which does not contain the stabilizer.

(b) A composition comprising a polyurethane prepared from toluene diisocyanate and alkylene polyols and 1.0% by weight of 15-benzyl-7,15-diazadispiro[5,1,5,3]hexadecane-14,16-dione is more stable to sunlight, fluorescent sunlamps, black lights and fluorescent lights than the unformulated polyurethane.

(c) A composition comprising a polycarbonate prepared from bisphenol-A and phosgene and 1% by weight of 4-n-octadecyl-2,2,6,6-tetramethyl 3,5-diketopiperazine resists discoloration due to exposure to ultraviolet light longer than one which does not contain the stabilizer.

(d) A composition comprising a polyester (polyethyleneterephthalate) and 0.2% by weight of 15,15'-(2",3",5",6"-tetramethyl-p-xylilidenyl)bis(7,15-diazadispiro[5,1,5,3]hexadecane resists discolation due to exposure to ultraviolet light longer than one which does not contain the stabilizer.

(e) A composition comprising polymethylmethacrylate and 0.25% by weight of 15,15'-(2",3",5",6"-tetramethyl-p-xylilidenyl)bis(7,15-diazadispiro[5,1,5,3-]hexadecane resists discoloration due to exposure to ultraviolet light longer than one which does not contain the stabilizer.

EXAMPLE 9

(a) A stabilized linear polyethylene is prepared by incorporating therein 0.5% by weight of 4-benzyl-2,2,6,6-tetramethyl-3,5-diketopiperazine. The stabilized compositions resist embrittlement due to exposure to ultraviolet light longer than one which does not contain the stabilizer.

(b) A stabilized polyamide (nylon 6,6) is prepared by incorporating therein 0.1% of 15,n-octadecyl-7,15-diazadispiro[5,1,5,3]hexadecane-14,16-dione. The light stability of the stabilized composition is superior to that of an unstabilized polyamide.

(c) A stabilized polyphenylene oxide polymer (prepared by polymerizing 2,6-dimethylphenol) is prepared by incorporating therein 0.5% by weight 15,15'-(2",3",5",6-tetramethyl-p-xylilidenyl)bis(7,15-diazadispiro[5,1,5,3]hexadecane-14,16-dione. The stabilized compositions resist embrittlement due to exposure to ultraviolet light longer than one which does not contain the stabilizer.

(d) A stabilized crystalline polystyrene is prepared by incorporating therein 0.1% by weight of 4,4'-(2,4,6-trimethyl-α,α',α"-mesitylidene)tris-2,2,6,6-tetramethyl-3,5-diketopiperazine. The stabilized compositions resists embrittlement due to exposure to ultraviolet light longer than one which does not contain the stabilizer.

EXAMPLE 10

High impact polystyrene resin containing elastomer (i.e., butadiene-styrene) is stabilized against loss of elongation properties due to exposure to ultraviolet light by incorporation of 0.3% by weight of 15-n-octadecyl-7,15-diazadispiro[5,1,5,3]hexadecane-14,16-dione.

The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163° C. and a pressure of 2,000 pounds per square inch into a sheet of uniform thickness (25 mil). The sheets are then cut into strips approximately 4×0.5 inches. A portion of these strips is then measured for percent of elongation in the Instron Tensile Testing Apparatus (Instron Engineering Corporation, Quincy, Massachusetts). The remaining portion of the strips are placed in an FS/BL chamber according to Example 6 (b) except that the time to 50% reduction in elongation is measured. The stabilized polystyrene resin retains its elongation property longer than the unstabilized resin.

Similar results are obtained when an equivalent amount of the following stabilizers are used in place of the above mentioned stabilizer.

(a) 0.1% by weight of 15,15',15"-(2,4,6-trimethyl-α,α',α"-mesitylidene)tris(7,15-diazadispiro[5,1,5,3]hexadecane-14,16-dione (b) 0.2% by weight of 15,15'-n-octamethylene bis(7,15-diazadispiro[5,1,5,3]hexadecane-14,16-dione)

(c) 1.0% by weight of 15-methyl-7,15-diazadispiro[5,1,5,3]hexadecane-14,16-dione (d) 0.1% by weight of 4-n-octadecyl-2,2,6,6-tetramethyl-3,5-diketopiperazine (e) 0.1% by weight of 4,4'(2",3",5",6"-tetramethyl-p-xylilidenyl)bis(2,2,6,6-tetramethyl-3,5-diketopiperazine (f) 0.5% by weight of 4,4'(n-octamethylene)bis(2,2,6,6-tetramethyl-3,5-diketopiperazine (g) 1% by weight of 4-n-octyl-2,2,6,6-tetramethyl-3,5-diketopiperazine (h) 0.5% by weight of 15-n-octadecyl-1,9-dimethyl-7,15-diazadispiro[5,1,5,3]hexadecane-14,16-dione.

Antioxidants may also be incorporated into each of the above mentioned compositions for example, di-n-octadecyl-α,α'-bis(3-t-butyl-4-hydroxy-5-methylbenzyl) malonate 2,4-bis(4-hydroxy-3,5-di-t-butylphenoxy)-6-(n-octylthioethylthio)-1,3,5-triazine, 2,4-bis(3,5-di-t-butyl-hydroxyphenoxy)-6-(n-octylthio)-1,3,5-triazine di-n-octadecyl 3,5-di-t-butyl-4-hydroxybenzyl phosphonate and octadecyl 3(3',5"-di-t-butyl-4-hydroxyphenyl)-propionate respectively.

EXAMPLE 11

Outdoor Exposure Tests

The additives were solvent blended onto polypropylene powder (Hercules Profax 6501) in the indicated amounts, the powder was agitated for 5 minutes in a Kitchen Aid planetary mixer and the powder mixture was dried in a vacuum oven at a vacuum of 30 inches of water overnight.

The polypropylene powder containing the additives was extruder compounded at 232° C. into pellets, and the pellets were melt spun at 260° C. into 15 denier monofilaments using a 10 mil orifice monofilament spinerett. The monofilaments were air cooled and oriented at a 4:1 ratio between hot (125° C.) and cold godets and wound onto a fiber spool. The monofilament was mounted on wooden exposure frames and exposed at 45° south direct weathering inland in Florida. Samples were removed from exposure periodically and tensile tested in the Instron Table Model tensile tester using fiber grips. The kilolangleys to 50% retention of tensile strength of the monofilament were determined.

The results indicated below show the number of kilolangleys (KL) to 50% retention of tensile strength. A Langley is a measure of energy in the ultraviolet region to which the samples have been exposed.

Table III

| Formulation* | KL to 50% Retention of Tensile Strength |
|---|---|
| 0.5% of 15-n-octadecyl-7,15-diazadispiro[5,1,5,3]hexadecane-4,16-dione | 69 |
| 0.5% of 15-benzyl-7,15-diazadispiro[5,1,5,3]hexadecane-14,16-dione | 81 |
| Control* | 36 |

*Each of the sample tests and the control contain 0.5% of the antioxidant dioctadecyl(3,5-di-t-butyl-4-hydroxybenzyl)phosphonate and 0.1% of the buffer calcium stearate.

What is claimed is:

1. A compound of the formula

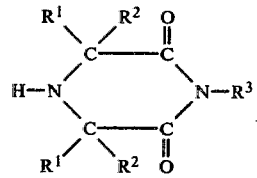

wherein $R^1$ and $R^2$ are independently of each other methyl or ethyl, and $R^3$ is benzyl.

2. A compound according to claim 1 which is 4-benzyl-2,2,6,6-tetramethyl-3,5-diketopiperazine.

* * * * *